US012633070B2

(12) United States Patent
Littlefield et al.

(10) Patent No.: US 12,633,070 B2
(45) Date of Patent: *May 19, 2026

(54) CUSTOM HEADWEAR MANUFACTURED BY ADDITIVE MANUFACTURE

(71) Applicant: CRANIAL TECHNOLOGIES, INC., Tempe, AZ (US)

(72) Inventors: Timothy R Littlefield, Phoenix, AZ (US); Jerold N Luisi, Phoenix, AZ (US); George E Kechter, Peoria, IL (US)

(73) Assignee: CRANIAL TECHNOLOGIES, INC., Tempe, AZ (US)

( * ) Notice: Subject to any disclaimer, the term of this patent is extended or adjusted under 35 U.S.C. 154(b) by 663 days.

This patent is subject to a terminal disclaimer.

(21) Appl. No.: 17/180,180

(22) Filed: Feb. 19, 2021

(65) Prior Publication Data

US 2021/0268790 A1 Sep. 2, 2021

Related U.S. Application Data

(63) Continuation of application No. 16/925,700, filed on Jul. 10, 2020, now Pat. No. 11,776,228, which is a
(Continued)

(51) Int. Cl.
*G06T 19/20* (2011.01)
*A61F 5/058* (2006.01)
(Continued)

(52) U.S. Cl.
CPC .......... *G06T 19/20* (2013.01); *A61F 5/05891* (2013.01); *B29C 64/386* (2017.08);
(Continued)

(58) Field of Classification Search
CPC .............. A61F 5/05891; B29C 64/386; B29K 2105/04; B29L 2031/4807; B33Y 30/00;
(Continued)

(56) References Cited

U.S. PATENT DOCUMENTS 5,094,229 A 3/1992 Pomatto et al.
5,308,312 A 5/1994 Pomatto et al.
(Continued)

FOREIGN PATENT DOCUMENTS

WO WO-2017042550 A1 * 3/2017 ......... A61F 5/05891

OTHER PUBLICATIONS

PCB Piezotronics, Sep. 8, 2016.*
(Continued)

*Primary Examiner* — Alireza Nia
*Assistant Examiner* — Andrew Jun-Wai Mok
(74) *Attorney, Agent, or Firm* — Donald J Lenkszus

(57) ABSTRACT

Custom manufactured headwear for a subject's head is provided. The headwear comprises an inner layer shaped to contact the head of the subject at predetermined areas. The inner layer is deposited by an additive manufacturing device. The headwear further comprises an outer layer deposited by the additive manufacturing device. The inner layer and the outer layer are each formed by the additive manufacture device utilizing a device data file derived from a subject data file. The subject data file is representative of the shape of the head and the device data file determining the shape of the headwear.

19 Claims, 6 Drawing Sheets

Related U.S. Application Data continuation of application No. 15/474,684, filed on Mar. 30, 2017, now Pat. No. 10,710,356.

(51) Int. Cl.

| | |
|---|---|
| *B29C 64/386* | (2017.01) |
| *B29K 105/04* | (2006.01) |
| *B29L 31/48* | (2006.01) |
| *B33Y 30/00* | (2015.01) |
| *B33Y 50/00* | (2015.01) |
| *B33Y 50/02* | (2015.01) |
| *B33Y 80/00* | (2015.01) |

(52) U.S. Cl.

CPC .............. *B33Y 30/00* (2014.12); *B33Y 50/00* (2014.12); *B33Y 50/02* (2014.12); *B33Y 80/00* (2014.12); *B29K 2105/04* (2013.01); *B29L 2031/4807* (2013.01); *G06T 2210/22* (2013.01); *G06T 2210/41* (2013.01); *G06T 2219/2016* (2013.01)

(58) Field of Classification Search

CPC ......... B33Y 50/00; B33Y 50/02; B33Y 80/00; G06T 2210/22; G06T 2210/41; G06T 2219/2016

See application file for complete search history.

(56) References Cited

U.S. PATENT DOCUMENTS

| | | | | |
|---|---|---|---|---|
| 5,666,670 | A | 9/1997 | Ryan | |
| 6,340,353 | B1* | 1/2002 | Pomatto | A61F 5/05891 |
| | | | | 602/17 |
| 6,423,019 | B1 | 7/2002 | Papay | |
| 6,592,536 | B1 | 7/2003 | Argenta | |
| 10,016,941 | B1 | 7/2018 | Beard | |
| 10,463,525 | B2* | 11/2019 | Littlefield | A61B 5/11 |
| 2004/0197016 | A1* | 10/2004 | Littlefield | G01N 29/28 |
| | | | | 382/128 |
| 2006/0010559 | A1 | 1/2006 | Hamlet | |
| 2006/0101559 | A1 | 5/2006 | Moore | |
| 2009/0316965 | A1 | 12/2009 | Mailling | |
| 2011/0132379 | A1 | 6/2011 | Lee | |
| 2012/0195994 | A1* | 8/2012 | El-Siblani | B29C 64/357 |
| | | | | 15/320 |
| 2013/0289459 | A1* | 10/2013 | Bernardoni | A61F 5/05891 |
| | | | | 602/17 |
| 2014/0201889 | A1* | 7/2014 | Pietrzak | G05B 19/4099 |
| | | | | 2/410 |
| 2014/0256209 | A1 | 9/2014 | Norman | |
| 2014/0274456 | A1 | 9/2014 | Cardani | |
| 2014/0371897 | A1 | 12/2014 | Lin | |
| 2015/0057784 | A1 | 2/2015 | Butler | |
| 2015/0210007 | A1 | 7/2015 | Durand | |
| 2015/0230959 | A1* | 8/2015 | Gilmer | A61F 5/05883 |
| | | | | 602/17 |
| 2015/0313305 | A1* | 11/2015 | Daetwyler | A63B 71/10 |
| | | | | 2/414 |
| 2016/0349738 | A1* | 12/2016 | Sisk | B29C 64/386 |

OTHER PUBLICATIONS

3D Printing Aids Babies Healing from Flat Head Syndrom, https://3dprint.com/84519/3d-print-helmets-flat-head/, 3D Printing, Published Jul. 27, 2015.

Osteo3d Makes a Difference with 3D Printed Helmet for 5-Month-Old craniosynostosis Patient, https://3dprint.com/97581/osteo3d-3d-printed-helmet/, Published Sep. 25, 2015.

https://3dprintingindustry.com/news/now-can-3d-print-memory-foam-34265/, Now You Can 3D Print With Memory Foam, Oct. 8, 2014.

https://govinfo.gov/content/pkg/FR-2015-05-21/pdf/2015-11756. pdf, 49 CFR Part 571, pp. 29458-29486; DOT.

https://www.shapeways.com/blog/archives/408-3d-printing-virus-for-sti-file-type.html, Apr. 1, 2010.

Profis, Sharon,DIY:3D printing custom iPhone case,Jul. 31, 2012,retrieved on Aug. 8, 2019,; DIY3D (Year: 2012).

https://www.mcortechnologies.com/trends-3d-scan-print-applications-blog_trashed/; Mar. 23, 2015; Retrieved Sep. 17, 2019 (Year: 2015).

Maundy, How to create your own 3D printed iPhone case, Published Apr. 5, 2012, Retrieved on Jan. 25, 2020 (Year: 2012).

* cited by examiner

CUSTOM HEADWEAR MANUFACTURED BY ADDITIVE MANUFACTURE

This application is a continuation of U.S. patent application Ser. No. 16/925,700 filed Jul. 10, 2020 which is a continuation of Ser. No. 15/474,684 filed Mar. 30, 2017, now U.S. Pat. No. 10,710,356. This application is related to U.S. Pat. Nos. 10,846,925; 10,703,084; 10,726,617; 10,463, 525; 10,561,521; 10,603,203; and 10,682,846. This application is particularly related to U.S. Pat. No. 10,463,525. All the aforesaid Applications and Patents being owned by the Assignee of this invention.

The present invention pertains to custom cranial remodeling devices custom manufactured for subject patients and methods of manufacturing such devices.

The applicant of the present invention has pioneered the treatment of plagiocephaly in infants through the use of cranial remodeling devices that are each custom manufactured for each infant patient and has pioneered the customized manufacture of such devices.

One method of manufacturing custom cranial remodeling devices comprises capturing a three-dimensional digital image of the entirety of a patient's head to produce a digital file of the entire head, processing the digital file to generate a second digital file that represents a three-dimensional digital image of the entirety of a desired head shape for the patient, fabricating a life size model of the desired head shape, vacuum thermo-forming a foam liner onto the life size model, vacuum thermo-forming a hard plastic onto the foam liner, generating trim lines for the device, projecting the trim lines onto the hard plastic, cutting the trim lines, and manually finishing the trimmed cranial remodeling device.

Each different step in a manufacturing process presents the possibility of introduction of error or inaccuracy. Accordingly, it is desirable to reduce the number of steps to manufacture custom cranial remodeling devices.

In addition, a clinician typically captures the three-dimensional digital image of the entirety of a patient's head at a clinic and the manufacturing steps occur at one or more other physical locations. Because of the physical separation of the clinic and the manufacturing locations, the custom cranial remodeling device must be shipped from the manufacturing facility to the clinic resulting in a time delay that is measured in days.

Accordingly, it is also desirable to provide point of service manufacturing of cranial remodeling devices such that the manufacture occurs at the clinic location.

Optimally it is desirable to change out cranial remodeling devices frequently. By adding a foam liner, the cranial remodeling devices could be adjusted by a clinician to accommodate for the patient's growth. The foam liner is provided to extend the life of the product.

In addition, the inside foam liner does not always compress evenly under vacuum. When released from vacuum, there is some spring back of the material. The result of the spring back may result in the foam layer not retaining conformance to the model.

Accordingly, it is also desirable to manufacture cranial remodeling devices that are so accurately manufactured and easily manufactured such that it is not necessary to include a foam layer.

SUMMARY

An embodiment of apparatus to provide point of service manufacture of a custom cranial remodeling device for correction of cranial deformity of a subject comprises apparatus disposed at a physical location for capturing three-dimensional digital data of the head of the subject and generating a three-dimensional digital data file representative of the head; an additive manufacture device located at the same physical location; a processor that operates to process the three-dimensional digital data file to produce a device file comprising the shape for the custom cranial remodeling device and to provide the device file to the additive manufacture device. The additive manufacture device operates to utilize the device file to manufacture the custom cranial remodeling device at the physical location.

In various embodiments, the processor is located at one of the same physical location or at a location physically removed from the physical location.

In various embodiments, prior to providing device file to the additive manufacture device, the processor operates to modify the device file to include one or more removable manufacturing supports for the custom cranial remodeling device to facilitate additive manufacture of the custom cranial remodeling device.

In various embodiments, the processor operates to determine a plurality of different layers for incorporation into the cranial remodeling device and provides data for the different layers in the device file, and the additive manufacture device manufactures the custom cranial remodeling device with the plurality of different layers.

In the various embodiments, the processor automatically selects the plurality of different layers to comprise one or both of different strength and material properties.

In the various embodiments, the processor automatically selects the plurality of different layers to apply different forces over different areas of the head.

The processor may select the plurality of different layers such that none of the different layers comprises a foam layer.

In an embodiment, the processor operates to generate alignment marks in the device file for the additive manufacture device to print alignment marks on the custom cranial remodeling device to aide fitting the custom cranial remodeling device.

The processor may operate to select the plurality of different layers such that one of the different layers comprises a foam layer.

In an embodiment, the processor generates guidelines data in the device file, and the additive manufacture device utilizes the guidelines data to print guidelines on the custom remodeling device.

In various embodiments, the processor generates electronic sensor manufacture data in the device file, and the additive manufacture device utilizes the electronic sensor data to automatically manufacture one or more corresponding electronic sensors into the custom cranial remodeling device.

The processor may generate electronic sensor manufacture data in the device file for one or more electronic sensors operable to determine pressure applied to the head when the custom cranial remodeling device is worn on the head, and the additive manufacture device utilizes the electronic sensor data to automatically manufacture one or more corresponding electronic sensors into the custom cranial remodeling device.

In various embodiments, the processor generates electronic sensor manufacture data in the device file, the electronic sensor is operable to confirm that the custom cranial remodeling device is being correctly worn on the head, and the additive manufacture device utilizes the electronic sensor data to automatically manufacture one or more corresponding electronic sensors into the custom cranial remodeling device.

In various embodiments, the additive manufacture device may be utilized to automatically print one or more electronic transducers into the custom cranial remodeling device.

The one or more electronic transducers may be useable to determine one or more of tilt and turn of the head, whether the custom cranial remodeling device is being worn, and the frequency of predetermined head motions.

In various embodiments, the additive manufacture device automatically forms components integral with the custom cranial remodeling device. The components may comprise one or more of apparatus for fastening the cranial remodeling device in place on the head, electronic transducers, and electronic sensors.

In various embodiments, the processor identifies regions on the interior of the cranial remodeling device where one layer of the plurality of layers is to contact the head and other regions on the interior of the cranial remodeling device where the interior surface of the cranial remodeling device is to be spaced apart from the head. The additive manufacture device manufactures the cranial remodeling device with the regions and other regions.

An embodiment of a method for fabricating a custom cranial remodeling device for correction of cranial deformities in a subject, comprises: generating a three-dimensional digital data file for the subject at a clinic by capturing a three-dimensional data file representative of the head of the subject utilizing apparatus operating to capture three-dimensional data representative of the head, the apparatus located at the clinic; utilizing a processor to process the three-dimensional digital data file to produce a device file comprising the shape for the custom cranial remodeling device; and manufacturing the custom cranial remodeling device at the clinic by utilizing an additive manufacture device located at the clinic to operate with the three-dimensional digital data file.

In various embodiments, the method comprises providing the processor at one of the clinic or a location physically removed from the clinic.

In various embodiments, the method comprises modifying the digital data file prior to utilizing the additive manufacture device to include one or more removable manufacturing supports for the custom cranial remodeling device to facilitate additive manufacture of the custom cranial remodeling device.

In various embodiments, the method comprises utilizing the processor to determine a plurality of different layers for incorporation into the cranial remodeling device, and utilizing the additive manufacture device to manufacture the custom cranial remodeling device with the plurality of different layers.

In various embodiments, the processor automatically selects the plurality of different layers to comprise one or both of different strength and material properties.

The method may comprise automatically selecting the plurality of different layers to apply different forces over different areas of the head.

The method may further comprise selecting the plurality of different layers such that none of the different layers comprises a foam layer.

In various embodiments the method comprises utilizing the additive manufacture device to print alignment marks on the custom cranial remodeling device to aide fitting the custom cranial remodeling device.

The method may comprise selecting the plurality of different layers such that one of the different layers comprises a foam layer.

In various embodiments, the method comprises utilizing the additive manufacture device to print clinician guidelines on the custom remodeling device.

In various embodiments, the method comprises utilizing the additive manufacture device to print clinician guidelines on the custom cranial remodeling device.

In various embodiments, the method may comprise utilizing the additive manufacture device to print automatically print one or more electronic sensors into the custom cranial remodeling device.

In various embodiments, the method may comprise depositing one or more electronic sensors operable to determine the pressure level applied to the head when the custom cranial remodeling device is worn on the head.

In various embodiments, the method may comprise depositing one or more electronic sensors to confirm that the custom cranial remodeling device is being correctly worn on the head.

In various embodiments, the method may comprise utilizing the additive manufacture device to print to automatically print one or more electronic transducers into the custom cranial remodeling device.

In various embodiments, the one or more electronic transducers may be useable to determine one or more of tilt and turn of the head, whether the custom cranial remodeling device is being worn, and the frequency of predetermined head motions.

In various embodiments, the method may comprise utilizing the additive manufacture device to automatically form components integral to the custom cranial remodeling device.

In the various embodiments, the components comprise one or more of apparatus for fastening the cranial remodeling device in place on the head, electronic transducers, and electronic sensors.

In various embodiments, the method may comprise utilizing the processor to identify regions on the interior of the cranial remodeling device where one layer of the plurality of layers is to contact the head and other regions on the interior of the cranial remodeling device where the interior surface of the cranial remodeling device is to be spaced apart from the head.

In various embodiments, the method comprises locating apparatus for generating a three-dimensional digital data file for the subject at the clinic, locating the processor at the clinic, and locating the additive manufacture device at the clinic.

An embodiment of a point of service method at a clinic for fabricating a custom cranial remodeling device for correction of cranial deformities in a subject, comprises: generating a three-dimensional digital data file for the head of a subject located at the clinic by capturing a three-dimensional data file representative of the head utilizing digital image capture apparatus located at the clinic; utilizing, at the clinic, a processor to process the three-dimensional digital data file at the clinic by: automatically processing the scan data file to generate contour lines for the custom cranial remodeling device on the scanned head, automatically processing the scan data file to generate a modified head shape data file, juxtaposing the modified head shape with the scanned head shape having the contour lines, utilizing the modified head shape data file to generate a shape for a desired copolymer cranial remodeling band, projecting lines outward from the contour lines to the outer surface of the desired copolymer cranial remodeling device, and utilizing the contour lines to produce a device file comprising the shape for the custom cranial remodeling device. The method further comprises manufacturing the custom cranial remodeling device at the clinic by utilizing an additive manufacture device located at the clinic.

An embodiment of a method for fabricating a cranial remodeling device for correction of cranial deformities in a subject comprises generating a three-dimensional head data file for the head of the subject; identifying predetermined anthropometric reference points on the head represented by the three-dimensional head data file; automatically utilizing the predetermined anthropometric reference points to calculate contour lines on the head represented by the three-dimensional head data file for the cranial remodeling device; automatically generating a modified head shape data file for the head; juxtaposing the modified head shape represented by the modified head shape data file with the head represented by the three-dimensional head data file having the contour lines thereon; utilizing the modified head shape data file to generate a shape for a desired of a cranial remodeling device, the shape having an interior surface to contact the head and an outer surface; projecting lines outward from the contour lines to the outer surface; and utilizing the projected lines to establish cranial remodeling device contour lines for the cranial remodeling device.

The method may further comprise generating a three-dimensional device data file comprising the contoured shape.

The method may further comprise providing the three-dimensional device data file to an additive manufacturing device.

The method may further comprise utilizing the additive manufacturing device to manufacture the cranial remodeling device from the three-dimensional device data file.

In various embodiments, the method may comprise utilizing a three-dimensional printer as the additive manufacturing device.

Embodiments of the method may comprise modifying the three-dimensional data file by automatically orienting the three-dimensional head data file to a predetermined plane by first automatically identifying two predetermined anthropometric points on the head and utilizing the two anthropometric points to form a horizontal plane to which the head is rotated to produce a standardized oriented head data file for an oriented head shape.

In various embodiments, the method may comprise determining predetermined reference points on the head, and automatically selective utilizing the predetermined reference points to calculate the contour lines.

The method may comprise generating a three-dimensional device data file comprising the contoured shape.

The method may further comprise providing the three-dimensional device data file to an additive manufacturing device.

The method may comprise utilizing the additive manufacturing device to manufacture the cranial remodeling device from the three-dimensional device data file.

In various embodiments, the method may comprise utilizing a three-dimensional printer as the additive manufacturing device.

In embodiments, the method comprises capturing digital data for the three-dimensional head data file from the head.

In embodiments, the method may comprise capturing the digital data with one of digital image capture apparatus and scanning apparatus.

An embodiment of a method for creating a device data file for use by a three-dimensional printer to print a cranial remodeling device for correction of a deformed head shape in an infant comprises: generating a three-dimensional data file of the deformed head shape; processing the three-dimensional data file to generate a three-dimensional modified data file for a modified head shape for the infant; utilizing the modified head shape to generate a device data file for a cranial remodeling device; automatically determining predetermined reference points on the captured deformed head shape; automatically utilizing the predetermined reference points to calculate contour lines on the deformed head shape; projecting lines outward from the contour lines to the outer surface of the modified head shape; and modifying the modified head shape represented by the device file by utilizing the projected lines to establish contour lines for the cranial remodeling device in the device file.

An embodiment of a method for fabricating a cranial remodeling device for correction of cranial deformities in a subject comprises: generating a three-dimensional head data file for the head of the subject; identifying predetermined reference points on the head represented by the three-dimensional head data file; automatically selectively utilizing the predetermined reference points to calculate contour lines on the head represented by the three-dimensional head data file for the cranial remodeling device; automatically generating a modified head shape data file for the head; juxtaposing the modified head shape represented by the modified head shape data file with the head represented by the three-dimensional head data file having the contour lines thereon; utilizing the modified head shape data file to generate a shape for a desired of a cranial remodeling device, the shape having an interior surface to contact the head and an outer surface; projecting lines outward from the contour lines to the outer surface; and utilizing the projected lines to establish cranial remodeling device contour lines for the cranial remodeling device.

Embodiments of the method may comprise generating a three-dimensional device data file comprising the contoured shape.

Embodiments of the method may comprise providing the three-dimensional device data file to an additive manufacturing device and utilizing the additive manufacturing device to manufacture the cranial remodeling device from the three-dimensional device data file.

Various embodiments of the method comprise modifying the three-dimensional data file by automatically orienting the three-dimensional head data file to a predetermined plane by first automatically identifying two predetermined anthropometric points on the head and utilizing the two predetermined anthropometric points to form a horizontal plane to which the head is rotated to produce a standardized oriented head data file for an oriented head shape.

Various embodiments comprise determining predetermined anthropometric points on the head, and automatically utilizing the predetermined anthropometric points to calculate the contour lines.

Various embodiments may comprise generating a three-dimensional device data file comprising the contoured shape.

Various embodiments may comprise capturing digital data for the three-dimensional head data file from the head.

Embodiments may comprise capturing the digital data with one of digital image capture apparatus and scanning apparatus.

A method for creating a device data file for use by a three-dimensional printer to print a cranial remodeling device for correction of a deformed head shape in an infant comprises: generating a three-dimensional data file of the deformed head shape; processing the three-dimensional data file to generate a three-dimensional modified data file for a modified head shape for the infant; utilizing the modified head shape to generate a device data file for a cranial remodeling device; automatically determining predetermined anthropometric points on the captured deformed head shape; automatically utilizing the predetermined anthropometric points to calculate contour lines on the deformed head shape; projecting lines outward from the contour lines to the outer surface of the modified head shape; and modifying the modified head shape represented by the device file by utilizing the projected lines to establish contour lines for the cranial remodeling device in the device file.

An embodiment of a custom cranial remodeling device to correct a deformed head of a subject comprises an inner layer shaped to contact the head of the subject at predetermined areas, the inner layer deposited by an additive manufacturing device, an outer layer deposited by the additive manufacturing device, and the inner layer and the outer layer are each formed by the additive manufacture device utilizing a device data file derived from a subject data file, the subject data file representative of the shape of the deformed head, the device data file determining the shape of the cranial remodeling device to correct the shape of the deformed head.

In an embodiment, the device data file is derived from the subject data file and a modified data file. The modified data file is derived from the subject data file and is representative of a modified head shape.

In an embodiment, the device data file is derived by one or more processors: determining contour lines for the custom cranial remodeling device on the deformed head shape utilizing the data file; juxtaposing a digital representation of the modified shape on the deformed head shape; projecting the contour lines outward from the deformed head onto the modified shape; and utilizing the contour lines to produce the device file.

In various embodiments the inner layer comprises portions positioned to contact the head at predetermined surface areas of the head.

In various embodiments, the inner layer comprises a plurality of separate portions, each portion configured to contact one of a corresponding plurality of areas on the head.

In various embodiments the cranial remodeling device comprises one or more removable manufacturing supports to facilitate additive manufacture of the custom cranial remodeling device.

In various embodiments of the cranial remodeling device at least one intermediate layer is provided between the inner layer and the outer layer. The intermediate layer deposited by the additive manufacturing device.

In the various embodiments, the inner layer, the outer layer and the intermediate layer each comprise one or both of different strength and material properties.

In various embodiments the cranial remodeling device comprises alignment marks deposited on the cranial remodeling device by the additive manufacture device, the alignment marks aide fitting the custom cranial remodeling device.

One embodiment comprises a plurality of different layers comprising the inner and outer layers and one or more intermediate layers, the plurality of layers comprising one or more of different strength properties, material properties, and configurations, each layer of the plurality of layers is deposited by the additive manufacturing device.

In various embodiments, at least one layer of the plurality of layers comprises a cellular configuration.

In at least one embodiment, at least one layer of the plurality of layers comprises carbon fibers integrated therein.

In various embodiments, one or more electronic sensors are manufactured by the additive manufacture device into the custom cranial remodeling device.

Certain embodiments may comprise one or more electronic sensors operable to determine pressure levels applied to the head when the custom cranial remodeling device is worn on the head. The one or more electronic sensors are manufactured into the custom cranial remodeling device by the additive manufacture device.

Embodiments may comprise one or more electronic sensors operable to confirm that the custom cranial remodeling device is being correctly worn on the head. The one or more electronic sensors are manufactured into the custom cranial remodeling device by the additive manufacture device.

Embodiments may comprise one or more electronic transducers manufactured into the custom cranial remodeling device by the additive manufacture device. The one or more electronic transducers may be useable to determine one or more of tilt and turn of the head, whether the custom cranial remodeling device is being worn, and the frequency of predetermined head motions.

Various embodiments may comprise components integrally formed with the custom cranial remodeling device by the additive manufacture device. The components may comprise one or more of apparatus for fastening the cranial remodeling device in place on the head, electronic transducers, and electronic sensors.

An embodiment of a custom headwear device to be worn on the head of a subject comprises: an inner layer shaped to contact the head of the subject at predetermined areas, the inner layer deposited by an additive manufacturing device; an outer layer deposited by the additive manufacturing device; and the inner layer and the outer layer are each formed by the additive manufacture device utilizing a device data file derived from a subject data file, the subject data file representative of the shape of the head.

In various embodiments of the custom headwear device, the device data file is derived by one or more processors: determining contour lines for the custom headwear device on the head shape utilizing the data file; projecting the contour lines outward from the deformed head onto the modified shape; and utilizing the contour lines to produce the device file.

In various embodiments of the custom headwear device, the inner layer comprises portions positioned to contact the head at predetermined surface areas of the head.

In various embodiments of the custom headwear device, the inner layer comprises a plurality of separate portions, each portion configured to contact one of a corresponding plurality of areas on the head.

In various embodiments of the custom headwear device, one or more removable manufacturing supports are deposited to facilitate additive manufacture of the custom headwear device.

Various embodiments of the custom headwear device comprise at least one intermediate layer between the inner layer and the outer layer, the intermediate layer deposited by the additive manufacturing device.

In various embodiments of the custom headwear device, the inner layer, the outer layer and the intermediate layer each comprise one or both of different strength and material properties.

Various embodiments of the custom headwear device comprise alignment marks deposited on the custom headwear device by the additive manufacture device, the alignment marks aide fitting the custom remodeling device.

Various embodiments of the custom headwear device comprise guidelines printed by the additive manufacture device on the custom remodeling device.

Various embodiments of the custom headwear device comprise a plurality of different layers comprising the inner and outer layers and one or more intermediate layers, the plurality of layers comprising one or more of different strength properties, material properties, and configurations.

In various embodiments of the custom headwear device, at least one layer of the plurality of layers comprises a cellular configuration.

In various embodiments of the custom headwear device, at least one layer of the plurality of layers comprises carbon fibers integrated therein.

Various embodiments of the custom headwear device comprise one or more electronic sensors manufactured by the additive manufacture device into the custom cranial remodeling device.

Various embodiments of the custom headwear device comprise one or more electronic sensors operable to determine pressure levels applied to the head when the custom headwear device is worn on the head; and the one or more electronic sensors are manufactured into the custom headwear device by the additive manufacture device.

Various embodiments of the custom headwear device comprise one or more electronic transducers manufactured into the custom headwear device by the additive manufacture device.

In various embodiments of the custom headwear device, the one or more electronic transducers are useable to determine one or more of tilt and turn of the head, whether the custom cranial remodeling device is being worn, and the frequency of predetermined head motions.

Various embodiments of the custom headwear device comprise components integrally formed with the custom cranial remodeling device by the additive manufacture device; and the components comprise one or more of apparatus for fastening the cranial remodeling device in place on the head, electronic transducers, and electronic sensors.

BRIEF DESCRIPTION OF THE DRAWING

The invention will be better understood by a reading of the following detailed description of embodiments of the invention in which like reference indicators designate like elements and in which.

DETAILED DESCRIPTION

Figure 1:
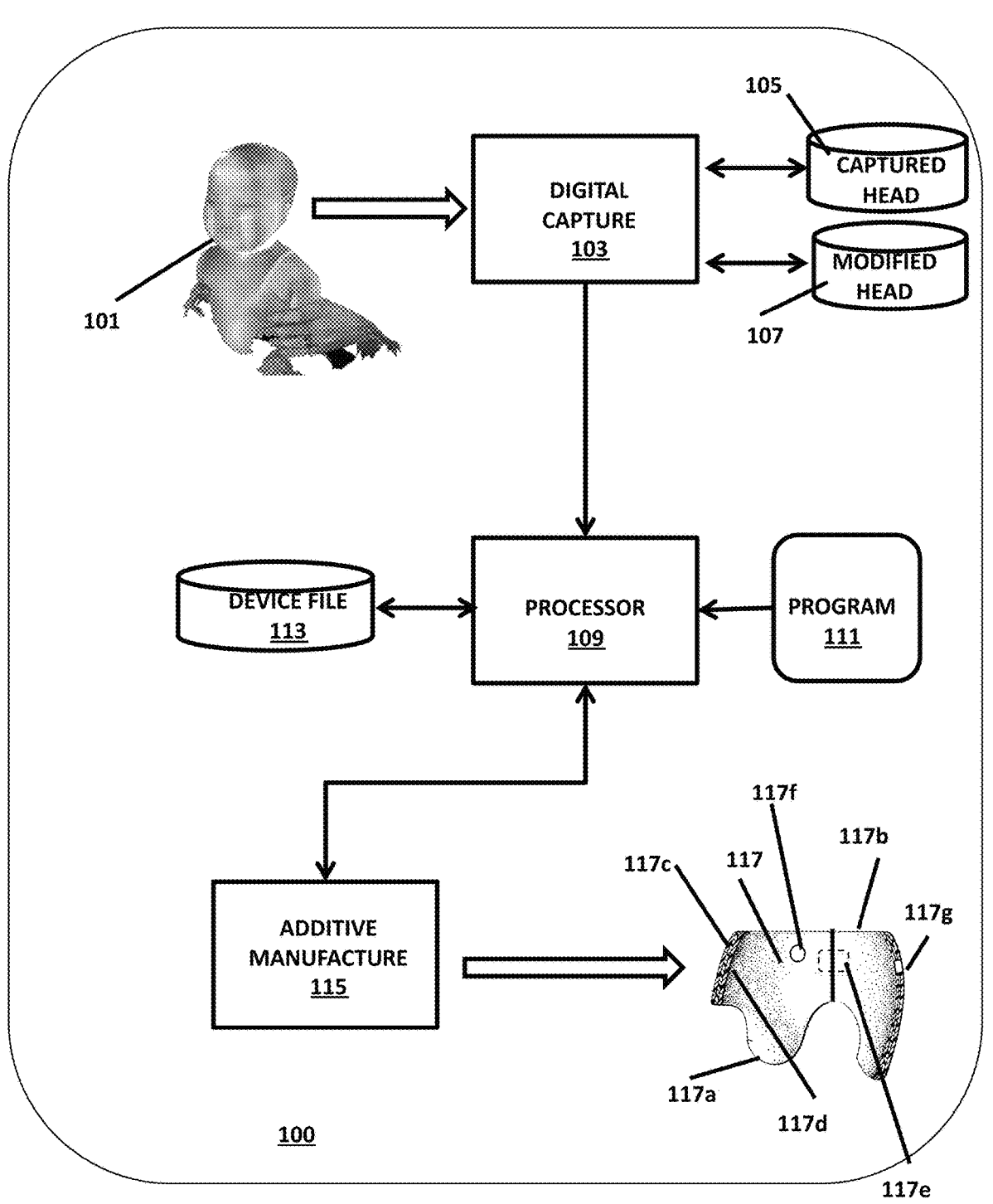
FIG. 1 illustrates an embodiment of a point of service manufacture facility.

Turning now to FIG. 1, a clinic 100 is shown provides a point of service manufacturing apparatus for the manufacture of cranial remodeling devices. At this point of service manufacture clinic, an infant 101 that has plagiocephaly has a three-dimensional digital image captured of its head by digital capture apparatus 103. Digital capture apparatus 103 may be one of a known apparatus that is used to capture three-dimensional digital images of the entirety of a head. For example, digital capture apparatus 103 may use a laser or other beam emitting scanner of a type described in U.S. Pat. Nos. 6,572,572 and 6,340,353, both of which are assigned to the assignee of this invention. Digital capture apparatus 103 may alternatively comprise optical capture apparatus such as that described in U.S. Pat. Nos. 7,142,701, 7,162,075, 7,245,743, 7,280,682, 7,305,369, 7,542,950, 8,103,088, and 8,217,993 all of which are also assigned to the assignee of this invention. The disclosures of all the above-listed patents are incorporated herein by reference.

Image capture apparatus 103 processes the captured data and generates a captured head data file 105 for the subject's head. In addition, image capture apparatus 103 processes data file 105 to generate a modified head data file 107. The head shape represented by modified head data file 107 represents a desired or corrected head shape for the subject. The methodology for generating the modified head shape data file is described in the above-identified patents and additionally in U.S. Pat. Nos. 8,442,288, 8,442,308, 8,472,686, 8,494,237, and 8,787,657 all of which are assigned to the assignee of this invention. The disclosures of these additional patents are incorporated herein by reference.

The captured head data file 105 and modified head data file are both accessed by processor 109 executing program 111 to generate a device data file 113 that completely defines a custom cranial remodeling device for subject 101. The operation of processor 109 executing program 111 is described in detail herein below.

Device data file 113 is provided to an additive manufacture device 115. Additive manufacture device 115 utilizes device data file 113 to manufacture a custom cranial remodeling device 117 for subject 101.

Additive manufacture device 115, in one embodiment is a commercially available three-dimensional printer that is operable to deposit layers of material to form cranial remodeling device 117. It will be recognized by those skilled in the art that there are various types of additive manufacture devices that are commercially available and the present invention encompasses those various types of additive manufacture devices.

The embodiment shown in FIG. 1 provides digital capture apparatus 103 and additive manufacture device 115 at the same physical location. In addition, processor 109 may also be located at the same physical location or located remotely from the clinic 100 and data linked thereto to provide the effect of being located at clinic 100.

It will be further appreciated by those skilled in the art that although a separate processor 109 is shown in FIG. 1, processor 109 is merely representative and may comprise one or more processors that are either located at clinic 100 or at a remote location or some combination thereof. Still further processor 109 may be incorporated into digital capture unit 103 such that the processor of digital capture unit also executes program 111 to generate device file 113.

Digital capture apparatus 103 operates on captured subject head data representing the digital image of the head of subject 101 to mathematically remove the subject's body and other extraneous information to establish a subject data file. The digital image of the subject's body is mathematically cropped or removed leaving just digital data representative of the digital image of the subject's head to provide three-dimensional cropped subject data.

The three-dimensional cropped subject data is oriented into a predetermined standardized orientation for further processing to produce a cropped and oriented data file that is referred to as the captured head data file 105.

It will be appreciated by those skilled in the art that in other embodiments, program 111 may provide the cropping and orientation functions that are provided by digital capture apparatus 103.

Processor 109, executing program 111, utilizes captured head data file 105 to generate curvature maps of the subject's head. A plurality of different types of curvature maps are generated by processor 109, executing program 111. Specific ones of the curvature maps are used to locate specific curvatures and features for a cranial remodeling device. Program 111 is utilized to create, reference, and cross-reference the curvature maps to determine an optimal position of a device contour.

The term "contour" as used herein is the shape that defines the what in the past has been called "trim lines" for cranial remodeling devices that were formed by first thermoforming foam and plastic layers onto a head model and then cutting or trimming the foam and plastic to a final shape of the cranial remodeling device to be worn on the head of a subject.

The program identifies anthropometric landmarks to determine the contour of the device.

In the embodiment described below, the cranial remodeling device 117 comprises outer surface 117c and inner surface 117d and further comprises bottom and top contour lines 117a, 117b. The bottom contour line 117a and the top contour line 117b are each calculated for cranial remodeling device 117 by processor 109 executing program 111 operating initially captured head data file 105. Cranial remodeling device 117 further comprises a fastener 117e to securely fasten the anterior and posterior portions together.

Figure 2:
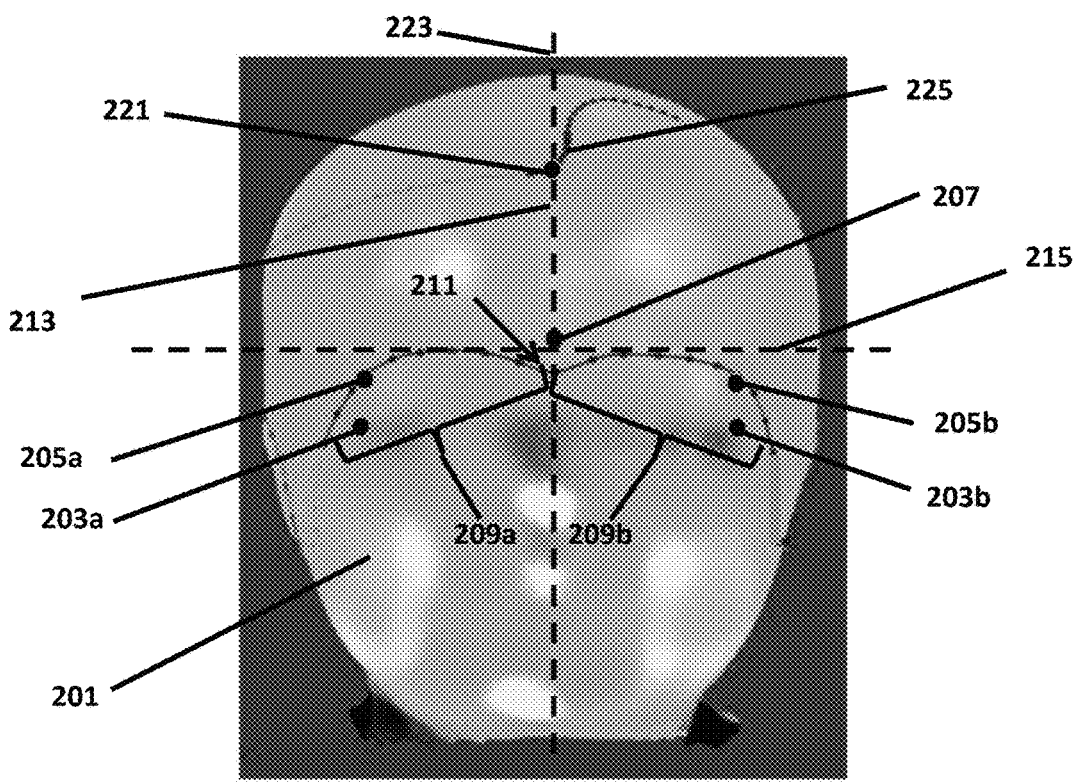
FIG. 2 is a screen shot of a frontal view of the head of a subject.
Figure 3:
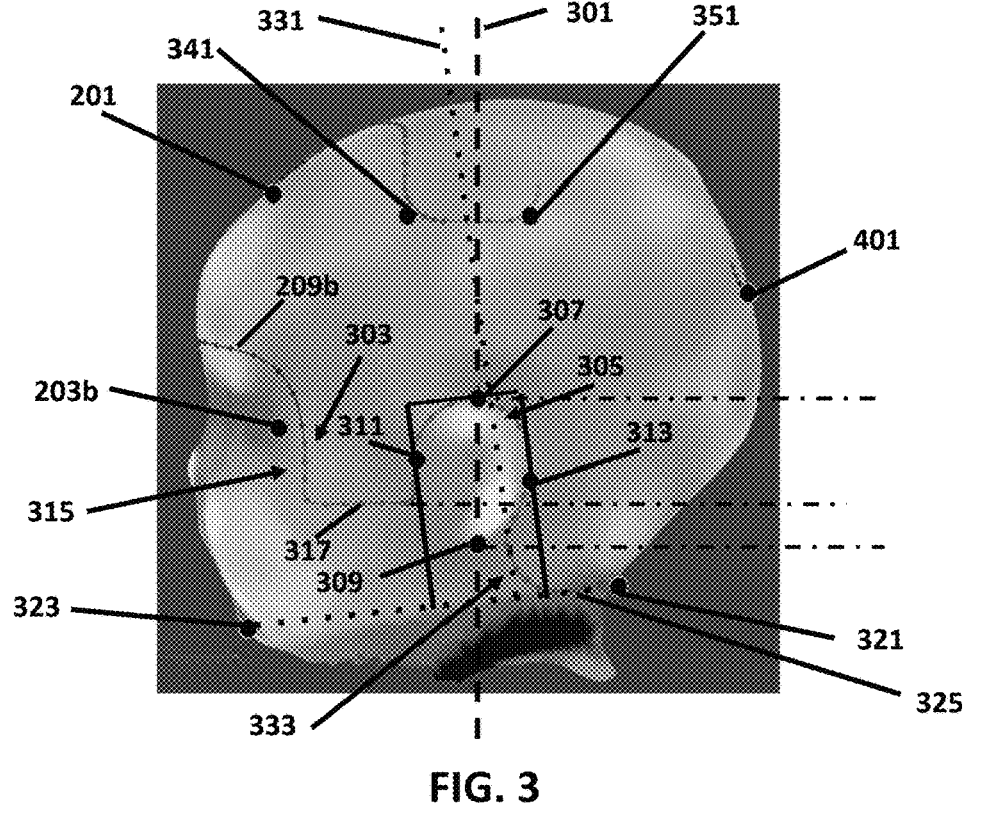
FIG. 3 is a screen shot of a left side view of the head of FIG. 2.

Turning now to FIGS. 2 and 3 execution of program 111 to calculate bottom contour line 117a is described first and then the execution of program 111 to calculate top contour line 117b is described.

FIG. 2 illustrates a curvature map 201 of a frontal view head of subject 101. Program 111 is executable to determine a bottom anterior contour line segments or splines by first mathematically defining two exocanthion locations 203a, 203b, the two frontozygomatics points 205a, 205b on the head, and the glabella 207. Using these five points 203a, 203b, 205a, 205b, 207 as a spatial reference, an elliptical cylinder shape is used to create the orbit contour splines 209a, 209b.

Program 111 executed by processor 109 identifies the sagittal plane 215 and uses sagittal plane 215 to identify the location of a key portion 211 of cranial remodeling device 117. In the embodiment, program 111 as executed by processor 109 generates a contour for key portion 211. Key portion 211 dips a predetermined distance below an orbital horizontal that is identified by program 111.

Turning now to FIG. 3, program 111 as executed by processor 109 identifies a coronal plane 301 on the head and anterior temporal extension lines 303a, 303b are attached to the ends of the orbital splines 209a, 209b at the exocanthions 203a, 203b and continue down parallel to coronal plane 301.

Program 111, executed by processor 109 generates ear contours or splines 305 for each ear. The location of ear contours 305 are determined by mathematically defining the top ear points 307, bottom ear points 309, front ear points 311 and back of ear points 313 and connecting the points 307, 309, 311, 313 for each ear with a curved spline 315. In addition to determining the ear contours 305, the midway point of the total length of the ear is defined.

The location, size and shape of the temporal piece contours 315 are determined by using the mathematically defined exocanthion points 203a, 203b and front ear points 311. The location of the bottom 317 of the temporal contour 315 is a predetermined portion x of the ears total length y above the bottom ear point 309.

Program 111, executed by processor 109, calculates a neck inflection portion of the contour. The location of the neck inflection contour portion is determined by using a mathematically defined neck inflection and the ears bottom points 309. The final location of the neck inflection point 321 is determined by calculating a weighted average between the mathematically defined neck inflection point and the ear bottom points 309.

Program 111, executed by processor 109, calculates an angle of the neck inflection contour is determined by calculating a guideline that connects the neck inflection point 321 to a chin point 323.

Program 111, executed by processor 109, calculates mastoid contours 331. The location, size and shape of the mastoid contours 331 are determined by using the mathematically defined ear points 307, 309, 311, 313, the neck inflection point 321 and chin point 323. A guideline 325 that connects the neck inflection point 321 to the chin point 323 is calculated. A line 331 perpendicular to the guideline 325 is placed a predetermined distance from the posterior ear point 313.

Curved contour portions 333 are each calculated, sized and positioned to be tangent to the back of the ear spline 305 and contact both the neck inflection point 321 to guide line 325 and line 331. The shape of each curved contour portion 333 is different for each head.

In the embodiment, cranial remodeling device 117 further comprises a top contour 117b.

Program 111, executed by processor 109, identifies a point 221 of low curvature on the sagittal midline 223 above the frontal bones as the location of an anterior superior contour.

Figure 4:
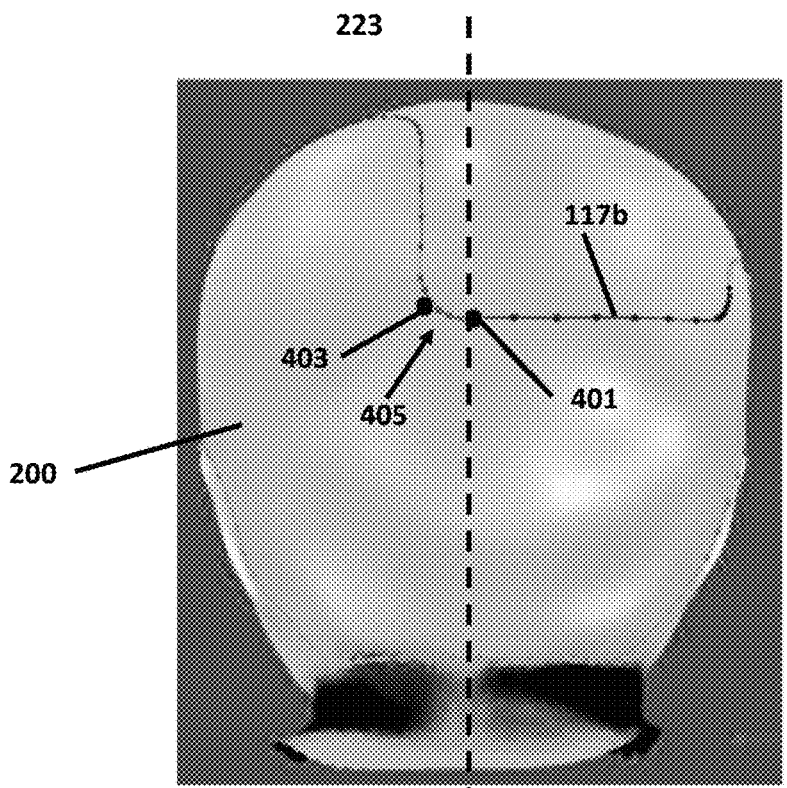
FIG. 4 is a screen shot of the rear of the head of FIG. 2.

Program 111, executed by processor 109, identifies a point 401 of low curvature on the sagittal plane 223 above the Occipital bones as the height location of the posterior superior as shown in FIG. 4.

Program 111, executed by processor 109, determines an anterior corner front starting point 225 from a standard offset of sagittal plane 223.

Program 111, executed by processor 109, determines an anterior corner lateral starting point 341 in the coronal direction utilizing curvatures associated with the coronal suture.

Program 111, executed by processor 109, determines a posterior corner back starting point 405 in the sagittal direction by calculating a standard offset of the mathematically derived sagittal plane 223.

Program 111, executed by processor 109, determines a posterior corner lateral starting point 351 in the coronal direction using the curvatures associated with the coronal plane 301.

Figure 5:
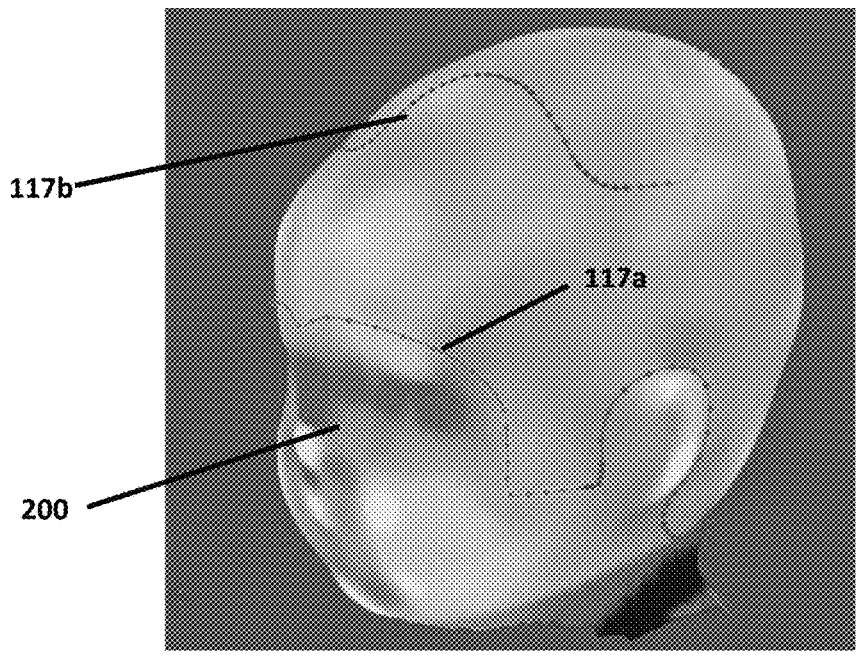
FIG. 5 is a screen shot of a perspective view of the head of FIG. 2 having contour lines thereon.

Program 111, executed by processor 109, by performing the above calculations and operations, defines top contour 117*b* and bottom contour 117*a* on the oriented head shape as shown in drawing figures and most clearly shown in FIGS. 1 and 5.

Figure 6:
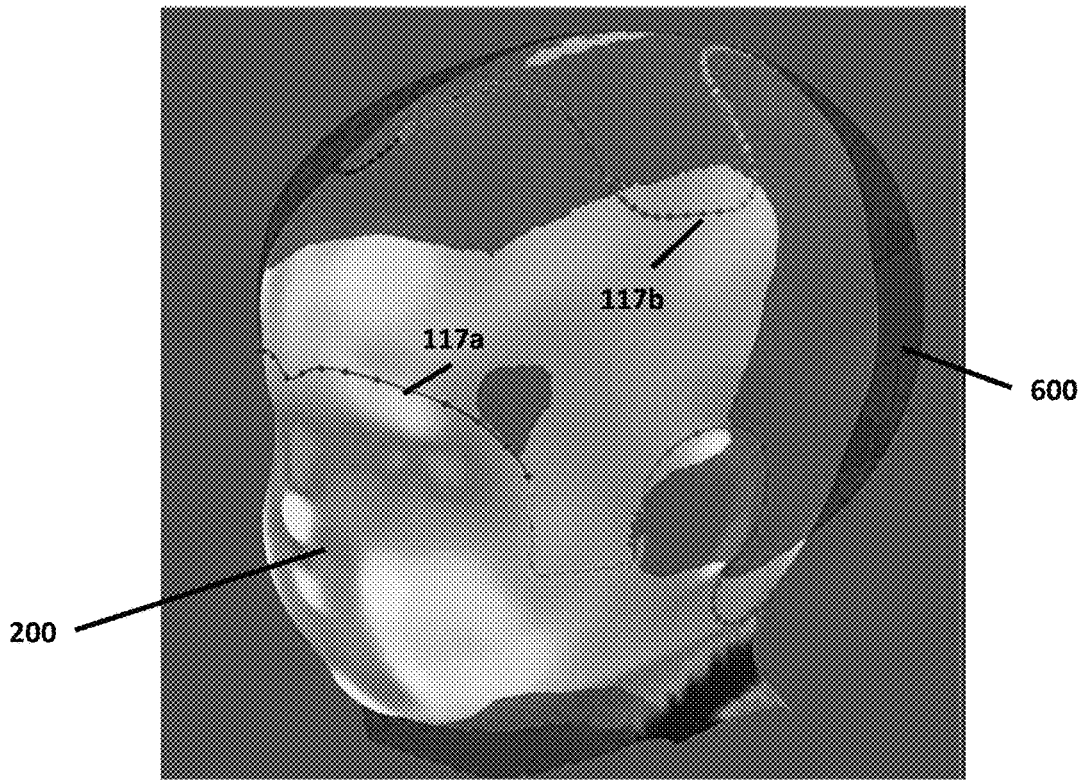
FIG. 6 is a screen shot of the perspective view of the head as shown in FIG. 5 having a modified head shape juxtaposed thereon.

Once the top and bottom contours 117*b*, 117*a* are created on the unmodified head shape, program 111, executed by processor 109, juxtaposes modified head shape 600 onto unmodified head shape 200 as shown in FIG. 6.

Program 111, executed by processor 109, utilized modified head shape 600 to generate a multilayered cranial remodeling device 700 juxtaposed onto modified head shape 600. At this point, multilayered cranial remodeling device 700 extends over substantially all of modified head shape 600 as shown in FIG. 7.

Figure 7:
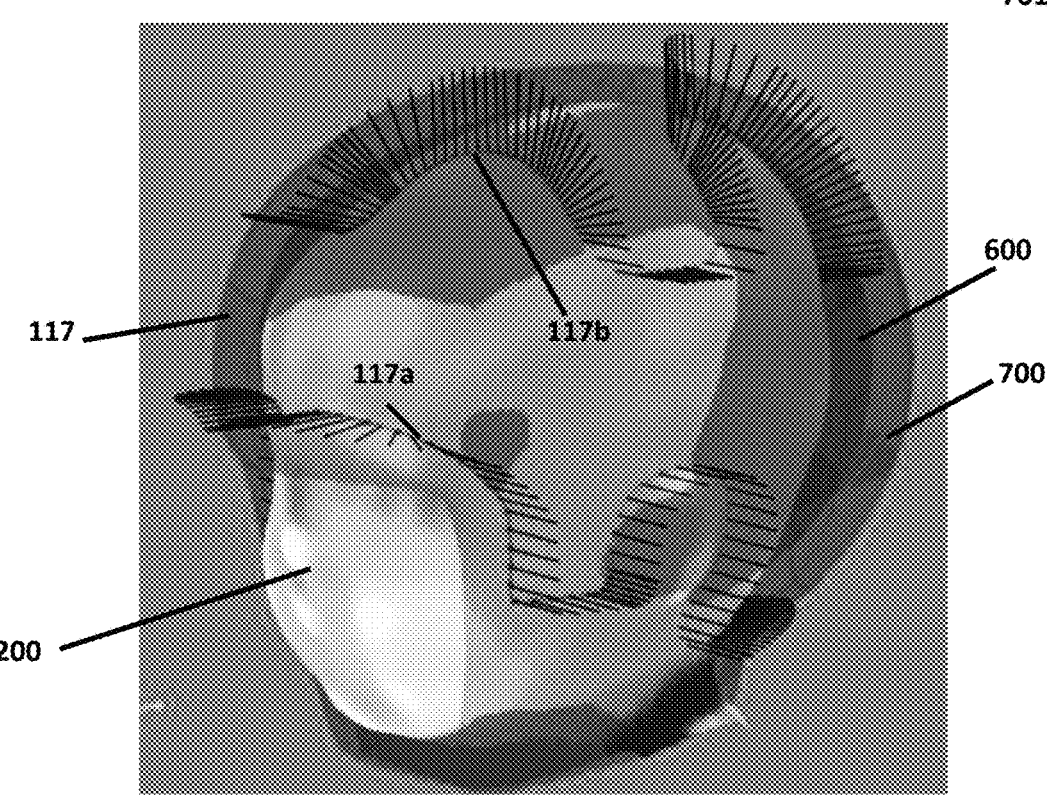
FIG. 7 is a screen shot of the perspective view of FIG. 6 further having an image of a cranial remodeling device thereon and lines projecting from the contour lines through the cranial remodeling device.

Program 111, executed by processor 109, projects lines 701 from top contour 117*b* and bottom contour 117*a* through juxtaposed modified head shape 600 and through juxtaposed multilayer cranial remodeling device 700 as shown in FIG. 7.

Figures 8, 9, 10:
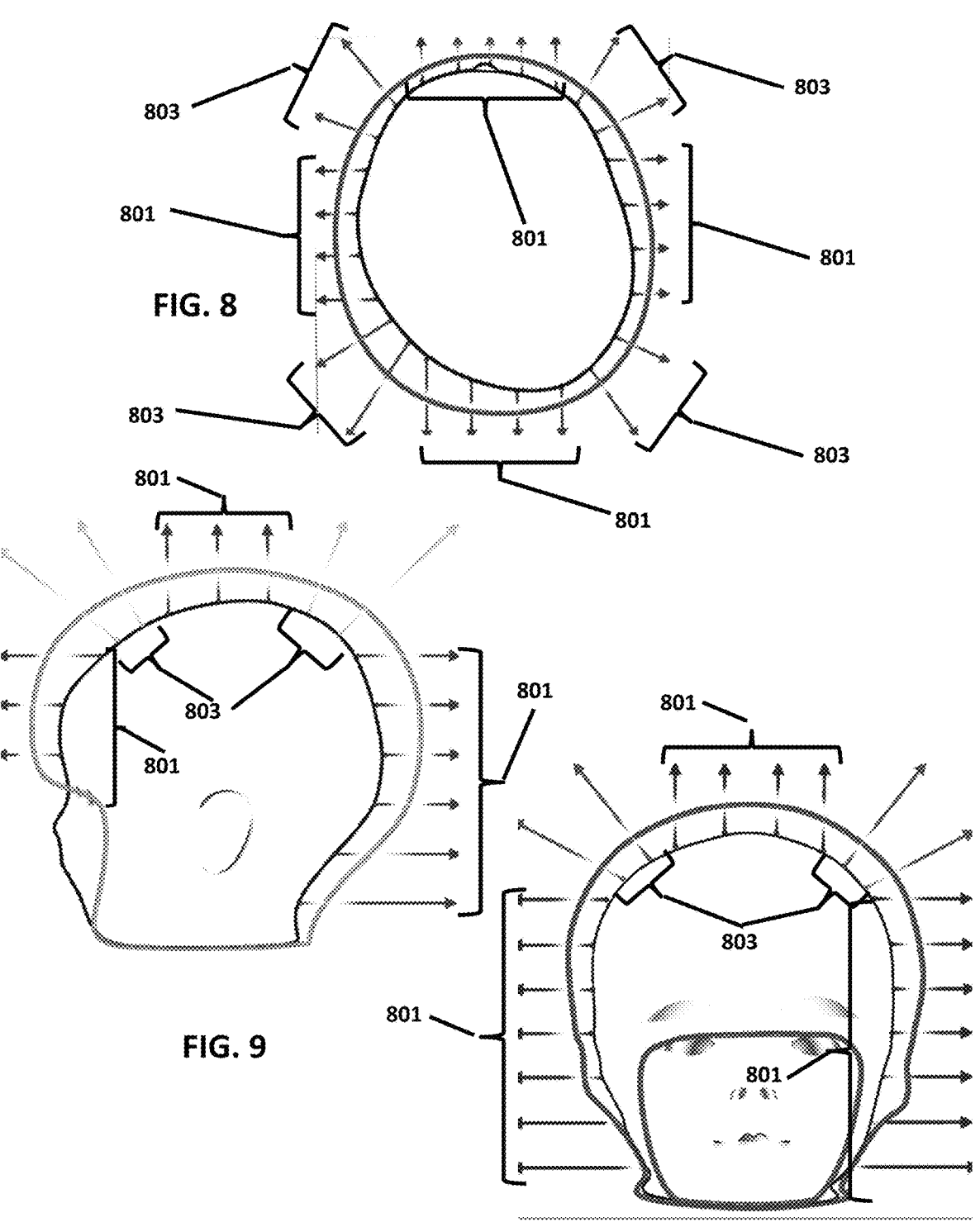
FIGS. 8, 9, and 10 illustrate the direction of the projecting lines of FIG. 7 from a top view, left side view and frontal view respectively.

Lines 701 are projected from unmodified head shape 200. As shown in FIGS. 8, 9, and 10, to maintain an optimal relationship to the modified head shape 600, lines 701 are projected directly right and left for lateral contours 801 and front/back for anterior and posterior contours 803. Where the right and left lines transition to the front and back lines 805 the projection of the lines is radial.

Program 111, executed by processor 109, utilizes projected lines 701 to define bottom and top contours 117*a*, 117*b* onto multilayered cranial remodeling device 700 to generate a device file 113.

In generating device file 113, program 111, executed by processor 109, selects the properties of each of a plurality of layers for the cranial remodeling device 117.

Figure 11:
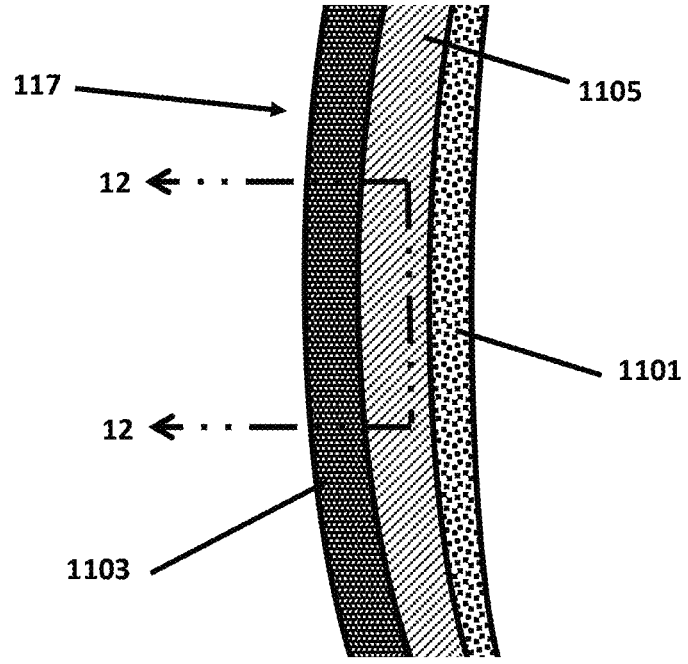
FIG. 11 is a cross section through a portion of an embodiment of a cranial remodeling device.

Additive manufacture device 115 of FIG. 1 utilizes device file 113 to manufacture a cranial remodeling device by depositing a plurality of layers as shown in FIG. 11. FIG. 11 is a cross-section of a portion of a cranial remodeling device 117 and is intended to be representative of embodiments of such a device. Other embodiments may have more or less layers deposited by additive manufacture.

One embodiment of a custom cranial remodeling device 117 to correct a deformed head of a subject comprises an inner layer 1101 shaped to contact the head of the subject at predetermined areas. The inner layer 1101 is deposited by additive manufacturing device 115 shown in FIG. 1. Cranial remodeling device 117 comprises an outer layer 1103 deposited by the additive manufacturing device 115. The inner layer 1101 and the outer layer 1103 are each formed by the additive manufacture device utilizing device data file 113 derived from a subject or captured head data file 105. The subject data file 105 is representative of the shape of the deformed head of the subject 101.

Device data file 113 determines the shape of the cranial remodeling device 117 to correct the shape of the deformed head.

In an embodiment, device data file 113 is derived from subject data file 105 and a modified data file 107. The modified data file 107 is representative of a modified head shape.

Device data file 113 is derived by one or more processors 109 operable to: determining contour lines 117*a*, 117*b* for custom cranial remodeling device 117*e* on the deformed head shape 200 shown in FIGS. 2 through 10; juxtaposing a digital representation 600 of the modified shape on the deformed head shape 200 as shown in FIGS. 6 and 7; projecting the contour lines 117*a*, 117*b* outward from the deformed head shape 200 onto the modified shape 600; and utilizing the contour lines to produce the device data file 113.

In various embodiments the inner layer comprises portions positioned to contact the head at predetermined surface areas of the head.

In various embodiments, inner layer 1101 comprises a plurality of separate portions that are not shown in the drawing figures. Each separate portion of inner layer 1101 is configured to contact one of a corresponding plurality of areas on the head shape 200.

In various embodiments, cranial remodeling device 117 comprises one or more removable manufacturing supports, that are not shown in the drawing figures, to facilitate additive manufacture of custom cranial remodeling device 117. The supports are provided solely to facilitate additive manufacture and are removed prior to utilization of cranial remodeling device 117. The supports may be of any convenient configuration and may be comprised from an additive material that is easily dissolved or is otherwise easily removable from the finished cranial remodeling device.

In various embodiments, the inner layer 1101, the outer layer 1103 and the intermediate layer 1105 each comprise one or both of different strength and material properties. Device data file 113 as generated by processor 109 executing program 111 automatically determines the material deposited for each layer 1101, 1103, 1105 and any configuration details for each layer 1101, 1103, 1105.

In various embodiments, cranial remodeling device 117 comprises alignment marks deposited on the cranial remodeling device 117 by additive manufacture device 115. The alignment marks aid a clinician in fitting custom cranial remodeling device 117 to subject 101. The alignment marks may be formed by incorporation of various landmarks such as depressions or protrusions or other identifications formed into a layer and visible to a clinician.

One embodiment comprises a plurality of different layers comprising inner layer 1101, outer layer 1103 and one or more intermediate layers 1105, the plurality of layers comprising one or more of different strength properties, material properties, and configurations, each layer 1101, 1103, 1105 of the plurality of layers is deposited by the additive manufacturing device.

Figure 12:
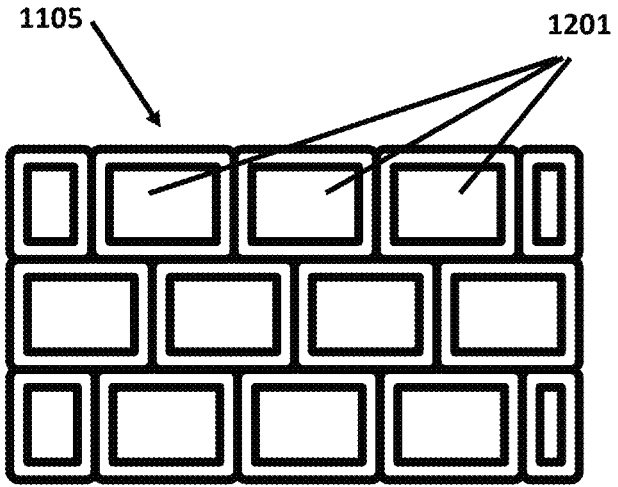
FIG. 12 is a cross section of a cranial remodeling device taken along lines 12-12 of FIG. 11.

In various embodiments, at least one layer of the plurality of layers comprises a cellular configuration as shown in FIG. 12. Although a rectangular cellular construction is shown in FIG. 12, it will be understood by those skilled in the art, that various configurations may be selected. By way of non-limiting example, the cellular construction may present a beehive cellular construction. The use of a cellular construction may present particular advantages for certain embodiments. For example, the use of a cellular construction may provide greater strength and a lighter weight cranial remodeling device.

In at least one embodiment, at least one layer of the plurality of layers comprises carbon fibers integrated therein. For example, outer layer 1103 may comprise carbon fibers to provide greater strength and lighter weight to cranial remodeling device 117.

By utilizing additive manufacture, one or more electronic sensors 117g may be embedded in cranial remodeling device 117 as part of the additive manufacture protocol presented by device data file 113.

The one or more electronic sensors 117g may be operable to determine pressure levels applied to the subject's head when custom cranial remodeling device 117 is worn.

The one or more electronic sensors 117g may further be operable to confirm that custom cranial remodeling device 117 is being correctly worn on the subject's head.

In other embodiments one or more electronic transducers 117f are manufactured into the custom cranial remodeling device 117 by the additive manufacture device 115. The one or more electronic transducers 117f may be useable to determine one or more of tilt and turn of the subject's head, whether the custom cranial remodeling device 117 is being worn, and the frequency of predetermined head motions.

Various embodiments may comprise components integrally formed with the custom cranial remodeling device 117 by the additive manufacture device 115. The components may comprise one or more of fastener apparatus 117e for fastening the cranial remodeling device in place on the head, electronic transducers 117f, and electronic sensors 117g.

Although the embodiments described above are for custom cranial remodeling devices, 117 other embodiments may be for custom headwear devices to be worn on the head of a subject. Embodiments of custom headwear devices may comprise: an inner layer 1101 shaped to contact the head of the subject at predetermined areas, the inner layer deposited by an additive manufacturing device; an outer layer 1103 deposited by the additive manufacturing device. The inner layer 1101 and the outer layer 1103 are each formed by the additive manufacture device 115 utilizing a device data file 113 derived from a subject or captured head data file 105. The subject data file 105 is representative of the shape of the head.

In various embodiments of the custom headwear device, the device data file is derived by one or more processors 109: determining contour lines 117a for the custom headwear device 117 on the head shape 200 utilizing device data file 113; projecting the contour lines 117a outward from the head as shown in FIG. 7; and utilizing the contour line 117 as to produce the device file. It will be apparent to those skilled in the art that if the custom headwear device 117 is not intended to be utilized for cranial remodeling, but, for example is a protective headwear device that there is no modified head shape 600 and the shape of the protective headwear device 700 is juxtaposed directly onto the subject head shape 200. The contour lines 117a are then projected outward as shown in FIG. 7 to provide contour lines for the protective headwear device and to generate the corresponding custom headwear device data for use by additive manufacture device 115.

In various embodiments of the custom headwear device 117, inner layer 1101 comprises portions positioned to contact the head at predetermined surface areas of the head.

In various embodiments of the custom headwear device, inner layer 1101 may comprise a plurality of separate portions, each portion configured to contact one of a corresponding plurality of areas on the subject's head.

In various embodiments of the custom headwear device 117, one or more removable manufacturing supports as described herein above are deposited to facilitate additive manufacture of the custom headwear device.

Various embodiments of the custom headwear device 117 comprise at least one intermediate layer 1105 between the inner layer 1101 and the outer layer 1103, the intermediate layer 1105 is deposited by the additive manufacturing device.

In various embodiments of the custom headwear device 117, the inner layer 1101, the outer layer 1103, and the intermediate layer 1105 each comprise one or both of different strength and material properties.

Various embodiments of the custom headwear device 117 comprise alignment marks as described herein above.

Various embodiments of the custom headwear device 117 comprise guidelines printed by the additive manufacture device on the custom headwear device as described herein above.

Various embodiments of the custom headwear device comprise a plurality of different layers comprising inner layer 1101, outer layer 1103, and one or more intermediate layers 1105, the plurality of layers comprising one or more of different strength properties, material properties, and configurations.

In various embodiments of the custom headwear device 117, at least one layer 1105 of the plurality of layers comprises a cellular configuration as shown in FIG. 12 and as described herein above.

In various embodiments of the custom headwear device 117, at least one layer of the plurality of layers comprises carbon fibers integrated therein.

Various embodiments of the custom headwear device 117 may comprise one or more electronic sensors 117g manufactured by the additive manufacture device into the custom headwear device 117.

Various embodiments of the custom headwear device comprise one or more electronic sensors 117g operable to determine pressure levels applied to the head when the custom headwear device is worn on the head; and the one or more electronic sensors are manufactured into the custom headwear device 117 by the additive manufacture device.

Various embodiments of the custom headwear device 117 comprise one or more electronic transducers 117f manufactured into the custom headwear device by the additive manufacture device.

In various embodiments of the custom headwear device 117, the one or more electronic transducers 117f are useable to determine one or more of tilt and turn of the head, whether the custom cranial remodeling device 117 is being worn, and the frequency of predetermined head motions.

Various embodiments of the custom headwear device 117 comprise components integrally formed with the custom cranial remodeling device 117 by the additive manufacture device; and the components comprise one or more of fastening apparatus 117e for fastening the cranial remodeling device in place on the head, electronic transducers 117f, and electronic sensors 117g.

In various embodiments, the methods and apparatus described for manufacture of cranial remodeling devices may also be used to manufacture custom headwear devices for subjects such as, by way of non-limiting example, sports helmets and protective helmets. In the manufacture of custom headwear devices, contour lines may be calculated on a captured subject data file representative of the shape of the subject's head that is captured utilizing one of digital image capture apparatus and scanning apparatus. The contour lines may be extended outward from the contour lines on the head image data representative of the subject's head through a calculated multi-layered headwear device juxtaposed onto the subject's head image data as described herein above.

The invention has been described in terms of various embodiments. It will be apparent to those skilled in the art that various modifications may be made without departing from the scope of the invention. It is intended that the invention be limited in scope only by the claims appended hereto.

The invention claimed is:

1. Custom manufactured headwear for a head of a current subject, comprising:

an inner layer comprising a first material shaped to contact said head of said current subject at predetermined areas;

an outer layer comprising a second material;

an intermediate layer comprising a third material disposed between said inner layer and said outer layer;

said inner layer, said intermediate layer, and said outer layer each comprise additive manufacturing apparatus deposited material;

each of said first material, said second material, and said third material having different characteristics from the others of said first material, said second material, and said third material;

each of said custom manufactured headwear, said inner layer, said intermediate layer, and said outer layer having shapes each defined by a device data file derived from a current subject data file, said current subject data file comprising a three-dimensional data file representative of an unmodified shape of said head of said current subject; and each of said inner layer, said intermediate layer and said outer layer comprising a peripheral edge having a shape defined by contour line data in said device data file, said contour line data determined directly from said current subject data file from calculated predetermined locations and calculated predetermined curvatures identified on said current subject head as represented in said current subject data file.

2. The custom headwear of claim 1, comprising:

said inner layer, said outer layer and said intermediate layer each comprise one or both of different strength properties, material properties, and configurations.

3. The custom headwear of claim 1, comprising:

said intermediate layer comprises cellular construction.

4. The custom headwear of claim 1, comprising:

said intermediate layer comprises fibers.

5. The custom headwear of claim 1, wherein:

at least one layer of said inner layer, said intermediate layer, and said outer layer comprises fibers.

6. The custom headwear of claim 1, comprising:

at least one of said inner layer, said intermediate layer, and said outer layer comprises carbon fibers.

7. The custom headwear of claim 1, comprising:

said inner layer comprises portions positioned to contact predetermined surface areas of said head of said current subject.

8. The custom headwear of claim 1, comprising:

said inner layer comprises a plurality of separate portions, each portion configured to contact one of a corresponding plurality of areas on said head of said current subject.

9. The custom headwear of claim 1, comprising:

one or more removable manufacturing supports to facilitate additive manufacture of said custom headwear.

10. The custom headwear of claim 1, wherein:

at least one of said inner layer, said intermediate layer, and said outer layer comprises cellular construction.

11. The custom headwear of claim 1, comprising: said inner layer comprises a plurality of portions arranged to contact said head of said current subject at a corresponding predetermined surface area of said head of said current subject.

12. The custom headwear of claim 1, comprising:

one or more of one or both of electronic sensors and transducers integrated into said custom headwear.

13. The custom headwear of claim 1, comprising: one or more of one or both of electronic sensors and transducers integrated into said headwear and operable to determine pressure levels applied to said head of said current subject when said headwear is worn on said head of said current subject.

14. The custom headwear of claim 1, comprising:

components integrally formed with said custom headwear, said components comprise one or more of electronic transducers and electronic sensors.

15. Custom manufactured headwear for a head of a current subject, comprising: an inner layer comprising a first material and shaped to contact said head of a current subject, said inner layer comprising additive manufacturing apparatus deposited material; an outer layer comprising a second material comprising additive manufacturing apparatus deposited material; an intermediate layer comprising a third material disposed between said inner layer and said outer layer, said intermediate layer comprising additive manufacture apparatus deposited material; each of said first material, said second material, and said third material having different characteristics from the others of said first material, said second material, and said third material: said inner layer, said intermediate layer, and said outer layer are each determined by a device data file derived from a current subject data file, said current subject data file comprising a three-dimensional data file representative of an unmodified shape of said head of said current subject; a shape of said custom manufactured headwear, and each of said inner layer, said intermediate layer, and said outer layer determined by said device data file; and each of said inner layer, said intermediate layer and said outer layer having a peripheral edge defined by contour line data in said device data file, said contour line data calculated directly from said three-dimensional data file of an unmodified shape of said head of said current subject and corresponding to contour lines on said head of said current subject.

16. The custom manufactured headwear of claim 15, wherein at least one of said intermediate and outer layers comprises fibers.

17. The custom manufactured headwear of claim 15, wherein:

one of said inner layer, said intermediate layer, and said outer layer comprises a cellular construction.

18. The custom manufactured headwear of claim 15, wherein:

said inner layer comprises a plurality of portions, each arranged to contact a corresponding predetermined surface portion of said head of said current subject.

19. The custom manufactured headwear of claim 15, wherein:

said periphery of each of said inner layer, intermediate layer and outer layer corresponds to said contour lines being extended outward through said inner layer, said intermediate layer, and said outer layer.

\* \* \* \* \*